United States Patent [19]

Farr et al.

[11] Patent Number: 5,438,069
[45] Date of Patent: Aug. 1, 1995

[54] GLUCOHYDROLASE INHIBITORS USEFUL AS ANTIDIABETIC AGENTS

[75] Inventors: Robert A. Farr, Loveland; Norton P. Peet, Cincinnati, both of Ohio

[73] Assignee: Merrell Dow Pharmaceuticals Inc., Cincinnati, Ohio

[21] Appl. No.: 84,269

[22] PCT Filed: Dec. 13, 1991

[86] PCT No.: PCT/US91/09387
§ 371 Date: Dec. 9, 1993
§ 102(e) Date: Dec. 9, 1993

[87] PCT Pub. No.: WO92/11867
PCT Pub. Date: Jul. 23, 1992

Related U.S. Application Data

[63] Continuation-in-part of Ser. No. 784,208, Oct. 28, 1991, abandoned, which is a continuation-in-part of Ser. No. 639,635, Jan. 10, 1991, abandoned.

[51] Int. Cl.$^6$ ............... A61K 31/00; A01N 43/04; C07H 15/00
[52] U.S. Cl. ........................... 514/1; 514/23; 536/17.2
[58] Field of Search ............ 514/1, 53, 114, 23; 435/22, 15; 424/117; 536/17.2

[56] References Cited

U.S. PATENT DOCUMENTS

| | | | |
|---|---|---|---|
| 4,205,068 | 5/1980 | Skyes et al. | 424/117 |
| 4,399,224 | 8/1983 | Flider et al. | 514/23 |
| 4,697,006 | 9/1987 | Ikenaka et al. | 536/17.2 |
| 4,946,830 | 8/1990 | Pulverer et al. | 514/23 |
| 4,962,097 | 10/1990 | Parsons et al. | 514/114 |
| 4,963,479 | 10/1990 | Chavez et al. | 435/22 |
| 4,988,682 | 1/1991 | Kozikowski | 514/1 |
| 5,032,505 | 7/1991 | Pierce et al. | 435/15 |
| 5,053,399 | 10/1991 | Kozikowski | 514/1 |
| 5,240,707 | 8/1993 | Farr et al. | 424/405 |
| 4,937,3909 | 6/1990 | Faug | 568/669 |

FOREIGN PATENT DOCUMENTS 0056194 12/1981 European Pat. Off. .
0089812 3/1983 European Pat. Off. .

OTHER PUBLICATIONS

Sandstrom et al., "Antiviral Therapy In AIDS", Published Sep. 1987, by AIDS Press Limited, see pp. 372–390.
Broader, S., "Retroviruses in Human Lymphoma/Leukemia" published 1985 by Tokyo/VVU Science Press (Utrecht), see pp. 277–288.
Drugs, vol. 34, issued Sep. 1987, Sandstrom et al, "Antiviral".
Miwa et al, eds., "Retroviruses in Human Lymphoma/Leukemia", pbulished 1985 by Japan Sci. Soc. Press, Tokyo/VNU, Sci. Press, pp. 277–288.
Tetrahedron, vol. 47, No. 36, pp. 7537–7550, 1991, (Peet et al.).
Tetrahedron Letters, vol. 31, No. 49, pp. 7109–7112, 1990 (Farr et al).
Hino et al, Journal of Antibiotics, Jul. 1985, p. 926, Studies of an Immunomodulator, Swainsonine.
Kino et al, Journal of Antibiotics, Jul. 1985, p. 936, Studies of an Immunomodulator Swainsonine.
Humphries et al, Proc. Natl. Acad. Sci. U.S.A., vol. 83, pp. 1752–1756 Mar. 1986, Cell Biology.
Humphries et al., Cancer Research 48, 1410–1415, Mar. 15, 1981.
Bernet et al, Helvetica Chimica Acta, vol. 62, Fase 7, pp. 2400–2403 (1979).
Tatsuta et al., Tetrahedron Letters, vol. 31, No. 8, 1171–1172, 1990.
Ogawa et al, J. Org. Chem. 1984, 49, 2594–2599.
Paulsen et al., Liebergs Ann. Chem. 1987, 439–445.

(List continued on next page.)

*Primary Examiner*—David A. Redding
*Assistant Examiner*—Louise N. Leary
*Attorney, Agent, or Firm*—William R. Boudreaux

[57] ABSTRACT

The invention provides the compounds 1,2-dideoxy-2-(hydroxymethyl)-1-(methylamino)-myo-inositol hydrochloride, 1,2-dideoxy-2-(hydroxymethyl)-1-(methylamino)-scyllo-inositol, 1,6-dideoxy-6-(hydroxymethyl)-1-(methylamino)-myo-inositol.

3 Claims, No Drawings

OTHER PUBLICATIONS

Yoshikawa et al, Chem. Pharm. Bull. vol. 36, 1988, pp. 3714–3717.

Bernet et al, Helvetica Chimica Acta, vol. 62, FASC. 6, pp. 1990–2001 (1979).

Kitagawa et al., Chem. Pharm. Bull. vol. 37, (2) 542–544 (1989) Kitagawa et al.

Sunkara et al., Biochemical and Biophysical Research Communications, vol. 148, No. 1, 1987, pp. 206–210.

Tyms et al, The Lancet, Oct. 31, 1987, p. 1026.

Yoshikawa, et al, Chem. Pharm. Bull., vol. 36, (1988) pp. 4236–4239.

Ogawa et al, J. Org. Chem, 1983, 48, pp. 1203–1207.

Ogawa et al, Carbohydrate Reserach, 144, (1985) pp. 155–162.

Karpas et al, Proc. Natl. Acad. Sci. USA, vol. 85, pp. 9229–9233, Dec. 1988.

Walker et al, Proc. Natl. Acad. Sci. USA, vol. 84, pp. 8120–1824, Nov. 1987.

GLUCOHYDROLASE INHIBITORS USEFUL AS ANTIDIABETIC AGENTS

This is a continuation-in-part of application Ser. No. 07/784,208, filed Oct. 28, 1991, now abandoned, which is a continuation-in-part of application Ser. No. 07/639,635, filed Jan. 10, 1991, now abandoned.

BACKGROUND OF THE INVENTION

Glycoprotein processing is a complex, poorly understood means by which the sugar groups of a previously glycosylated protein are "trimmed" or "processed" in a particular sequence to obtain a specific pattern of glycosylation. The specificity is important to a number of recognition processes and is the basis for cell-cell and cell-virus interactions. The trimming is accomplished by a set of highly specific enzymes which recognize particular sequences of sugars. One such enzyme, Glucosidase I, is responsible for cleaving the three terminal glucose residue in the oligosaccharide structure ($Glc_3Man_9GlcNAc_2$). Clearly, inhibitors of such an enzyme could be useful in treating diseases and conditions in which glycoproteins are involved.

Certain viruses including the retroviruses have, in addition to the usual vital capsid, an outer membrane of lipid and glycoprotein, similar to the membrane of ordinary cells. Indeed, the lipid of the vital membrane is probably derived directly from the membrane of a previously infected host cell; however, the glycoprotein of the viral membrane is unique to the virus itself and is coded for by the viral genome. Infection of a host cell by a glycoprotein coated virus initially relies on the interaction of various receptors on the host cell surface with the glycoprotein membrane envelope of the virus. Subsequently, the virus and cell membranes fuse and the virion contents are released into the host cell cytoplasm. Thus the glycoprotein envelope of the coated viruses plays an important role in both the initial interaction of the virion and the host cell and in the later fusion of the viral and host cell membranes.

Interference with the formation of the viral envelope glycoprotein could prevent the initial virus-host cell interaction or subsequent fusion or could prevent viral duplication by preventing the construction of the proper glycoprotein required for the completion of the viral membrane. Inhibitors of Glucosidase I may be valuable agents in the treatment of membrane-coated viral disease and metastatic tumors. S. P. Sunkara et al., Biochem and Biophys Research Commun. 148(1), 206 (1987); A. Karpas et al., Proc. Natl. Acad. Sci. USA, 85, 9229 (1977); B. D. Walker et al., Proc. Natl. Acad. Sci. USA, 84, 8120 (1987).

Tumor metastasis is also a process which relies on the cell surface glycoproteins of a traveling tumor cell to bind to the cell surface of a distant tissue. The binding and subsequent cell fusion relies extensively on the cell surface glycoprotein and clearly interfering with the proper development of cell surface glycoproteins would prevent or reduce tumor metastasis. Glucosidase I inhibitors are known to be useful in preventing tumor metastasis and thus applicants' novel compounds are potential antimetastatic agents.

SUMMARY OF THE INVENTION

This invention relates to novel alpha glucohydrolase inhibitors of formula I

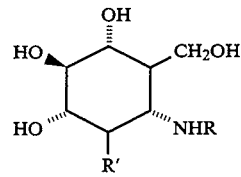

wherein
R is a hydrogen, a ($C_1$–$C_6$)alkyl optionally substituted with one or two hydroxy groups, a glycosyl group, or a group of the formula —$(CH_2)_n$—Ar wherein n is an integer of from 1 to 4 and Ar is a phenyl group optionally substituted with one or two groups selected from ($C_1$–$C_4$)alkyl, ($C_1$–$C_4$)alkoxy, F, Cl, Br, I, amino, mono($C_1$–$C_4$)alkyl- amino, or di($C_1$–$C_4$)alkylamino, and R' is hydrogen or an OR'' group wherein R'' is a hydrogen or a glycosyl group or a pharmaceutically acceptable salt thereof are Glucosidase I inhibitors and are useful in the treatment of viral infections and metastatic tumors.

DETAILED DESCRIPTION OF THE INVENTION

The usual stereochemical conventions are used throughout to denote the relative spatial orientation of groups attached to the rings. Thus, a solid line diverging from the point of attachment to a ring, indicates that the attached group is in the beta-configuration, that is, the group is above the plane of the ring. Likewise, a dotted line indicates that the attached group is in the alpha-configuration, that is, the group is below the plane of the ring. Attachment of a group to a ring by a normal, not divergent or dotted, line indicates that the spatial orientation can be either alpha or beta.

The ($C_1$–$C_6$)alkyl groups of this invention can be straight chained, branched chain or cyclic. Examples of such alkyl groups are methyl, ethyl, n-propyl, isopropyl, n-butyl, isobutyl, tert-butyl, n-pentyl, isopentyl, cyclopentyl, n-hexyl, and cyclohexyl.

In those alkyl groups substituted with two hydroxy groups, the hydroxy groups will not be bonded to the same carbon atom. Further, the hydroxy group will not be bonded to the carbon atom which is bonded to the amino nitrogen atom.

The glycosyl groups of this invention can be mono-, di- or trisaccharide moieties. The glycosyl group can be attached to the amino nitrogen atom through either an exocyclic or ring carbon atom of the glycosyl pentose or hexose ring thereby forming a variety of possible positional isomers for each individual glycosyl group. Also similar or dissimilar pentose or hexose moieties may be linked to each other through a glycosidic oxygen bridge wherein the bridging oxygen atom is attached to an exocyclic and/or endocyclic carbon atom of the pentose or hexose moiety of which the glycosyl radical is comprised; again all positional isomers are contemplated as within the scope of this invention.

Exemplary of glycosyl radicals contemplated are such monosaccharides as glucosyl, galactosyl, mannosyl, fucosyl, ribosyl, 2-deoxyglucosyl, 3-O-methylglucosyl, xylosyl, and arabinosyl, disaccharides as alpha- and beta-cellobiosyl, isomaltosyl, trehalosyl, and maltosyl, and such trisaccharides as maltotriosyl, and cellotriosyl. Particularly preferred are the compounds wherein R is mannosyl, glucosyl, L-fucosyl, N-acetylglucosyl, or cellobiosyl.

Acid addition salts with pharmaceutically acceptable acids referred to above are equivalent to the amines for the purposes of this invention. Illustrative of such salts are the salts with inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids; and with organic sulfonic acids such as methanesulfonic acid and p-toluenesulfonic acid. Such salts can be obtained by standard procedures from an amine of this invention and the appropriate acid.

Of those compounds of formula I, those compounds wherein R is a methyl or ethyl, a 2,3-dihydroxypropyl, 2-hydroxypropyl, glucosyl and mannosyl are preferred. Also preferred are those compounds of formula I wherein the hydroxymethyl group is in the beta-configuration. Further preferred are those compounds wherein the hydroxymethyl substituent is beta and R' is beta and wherein the hydroxymethyl substituent is beta and R' is alpha.

The compounds of formula I are prepared by protecting group removal from the compounds of formula II

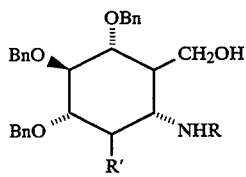

wherein R is as defined above. When R is an alkyl group, preferably the ring hydroxy groups are protected with benzyl groups (Bn) which can be removed in the usual manner such as by catalytic hydrogenation. Subsequently the amino group will be protected with a tert-butyloxycarbonyl group (Boc) which can be removed in the usual manner such as by mild acid hydrolysis conditions.

The compounds of formula II wherein the hydroxymethyl group is in the α-configuration, i.e., the compounds of formula IIa

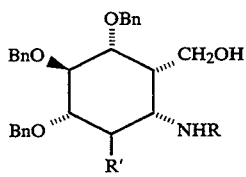

are prepared by the reduction of isoxazolidines of formula III

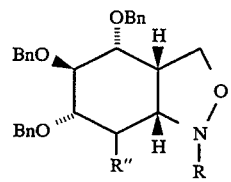

wherein R is $(C_1-C_6)$alkyl or $(CH_2)_n Ar$. The reduction can be accomplished by any means known to those skilled in the art for reduction of the oxygen-nitrogen bond provided that the reaction conditions do not substantially affect the relative stereochemistry of the groups. For example, a formula III compound can be reacted with an excess (2–5 molar) of activated zinc dust and an acid such as acetic acid. Typically this reaction is performed at a temperature of from about room temperature to about the reflux temperature of the mixture. The acid itself is usually the solvent and preferably will be an aqueous acetic acid solution such as an 85% aqueous acetic acid solution. The reaction will be substantially complete in from about one-half hour to about 2 or 3 hours.

The compounds of formula II wherein the hydroxymethyl group is in the β-configuration, i.e. the compounds of formula IIb,

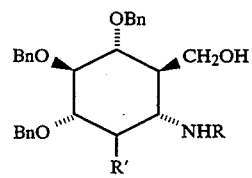

are prepared by an oxidation/epimerization/reduction sequence on the Boc derivative of the formula IIa compound prepared by treatment of the formula IIa compound with tert-butyloxycarbonyl anhydride ((Boc)$_2$O). The appropriate Boc derivative of the compound of formula IIa can be subjected to careful oxidation such as by treatment with the Dess-Martin periodinane. The resulting aldehyde of formula IVb

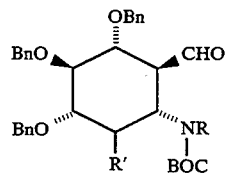

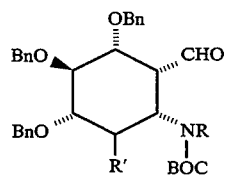

wherein the formyl group is in the alpha configuration can be treated with a non-nucleophilic base such as 1,8-diazabicyclo[5.4.0]undec-7-ene (DBU) at reduced temperature, preferably −78° C. to prevent elimination, which upon acidic workup results in the formula IVa aldehyde in which the formyl group is in the beta-configuration. Subsequent reduction of the aldehyde function with, for example, sodium borohydride and Boc group removal yields the desired compound of formula IIb.

The compounds of formula I wherein R is other than a $(C_1-C_6)$alkyl or $(CH_2)_n$Ar group can be prepared from the corresponding compound of structure I wherein R is hydrogen, which are prepared by treatment of the Boc derivatives of either IIa or IIb (R=p-methoxybenzyl) with ceric ammonium nitrate (CAN) in 4:1 $CH_3CN/H_2O$ for 1 hour at 0° C. to give IIa or IIb (R=Boc) followed by treatment with gaseous HCl or TFA to give, after neutralization, the IIa or IIb compound (R=H). Reductive amination with $NaBH_3CN$ and an aldehyde R'CHO wherein R' is a glycosyl moiety or protected hydroxyalkyl such as glyceraldehyde acetonide gives a compound of formula I or a protected derivative thereof. After any protecting groups are removed, e.g., aqueous acid if R'CHO is glyceraldehyde acetonide, the desired product of Formula I ($\beta,\beta$,configuration) is produced as described above.

To prepare those compounds of formula I wherein R is a glycosyl group, the appropriate compound of formula I wherein R is a hydrogen is treated with a appropriately hydroxy protected glycosyl halide, trillate, or other suitably activated derivative. This reaction can be acccomplished by, for example, heating the a mixture of the formula Ia and glycosyl compound in dry dimethylformamide (DMF) or other equivalently functioning solvent, at about 60°-90° C. for about 12 to 36 hours using excess amounts of a weak base such as potassium carbonate ($K_2CO_3$).

The intermediate compounds of formula III are prepared by an intramolecular cycloaddition of the transient product of the reaction of a hydroxlyamine, RNHOH wherein R is as defined above other than gylcosyl, with the appropriate aldehyde of formula IV

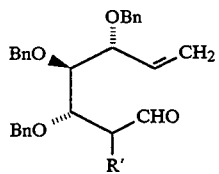

wherein R' is as defined above but is other than H. This reaction is performed by adding a solution of a slight molar excess (5–15%) of the hydroxylamine in a suitable solvent such as methanol to a stirred solution of the appropriate formula IV compound in a compatible solvent, typically methanol. The reaction mixture is heated, typically at the reflux temperature of the mixture for from about 1 to about 12 hours. Subsequently the product is concentrated by removing some of the solvent by employing a vacuum. Partial purification such as by flash chromatography gives the desired ring closed intermediate of formula III which can be used without further purification.

The preparation of the aldehydes of formula IV is within the skill of those of ordinary skill in the art. These compounds can be prepared by, for example, bromination of an appropriately protected O-methyl-glucopyranoside, followed by ring opening employing zinc dust, reaction with 1,3-dithiane and a base such as n-butyllithium followed by protection of the resulting hydroxyl group and routine hydrolysis of the dithiane moiety.

To prepare those compounds of formula III wherein R" is hydrogen a compound of formula IIIa

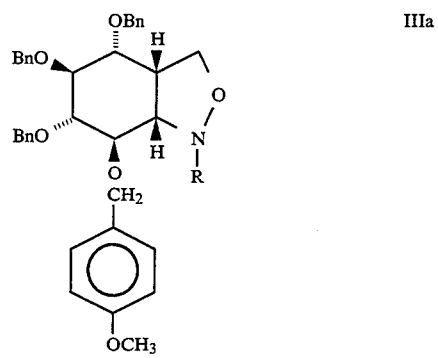

is treated under standard reaction conditions with DDQ or CAN which cleave the p-methoxybenzyl group to yield the corresponding hydroxyl compound III (R"=OH), and subsequent reduction of the corresponding O-alkyl-S-methyldithiocarbonate (Barton, D. H. R.; McCombie, S. W., *J. Chem. Soc. Perkin Trans. I* (1975), p. 1574, and Barton, D. H. R.; Jaszberenyi, J. C., *Tetrahedron Lett.* 30 (1989), p. 2619).

The ability of the compounds of this invention to act as $\alpha$-Glucosidase I inhibitors can be demonstrated by a microtiter plate assay using purified $\alpha$-Glucosidase I and [$^3$H]Glucose labelled substrate.

The [3H] glucose labelled oligosaccharides substrate ($G_3M_9N$) for Glucosidase I was prepared by metabolically labelling exponentially growing BHK cells with [$^3$H]galactose in the presence of 200 μg/ml of castanospermine. BHK cells grown as monolayer were treated with 200 μg/ml of castanospermine in DMEM (#430–1600) supplemented with 10% heat inactivated fetal calf serum, 2 mM L-glutamine and 1× of PSN antibiotic mixture. After a three hour incubation with castanospermine, [1-$^3$H]galactose (10 μci/ml of media) was added to label the glycoproteins and cells were allowed to grow to confluency for an additional 48 hours. At the end of the labelling period, the cells were washed with cold PBS and scraped with a rubber policeman. Cell pellet was heated for 10 minutes at 100° C. and exhaustively treated with pronase (usually 72 hours) in 50 mM Tris pH 7.5 containing 10 mM $CaCl_2$ and 1% Pronase under toluene atmosphere to obtain glycopeptides. The glycopeptides were separated on columns of Bio-gel P-4. The glycopeptide peak produced by castanospermine treatment was pooled, treated with Endo-H to release the oligosaccharides. The oligosaccharides obtained by endo-H hydrolysis were bound to a ConA column previously washed with buffer A (50 mM Tris pH 7.5 containing 500 mM NaCl) and equilibrated with buffer B (5 mM Sodium acetate buffer pH 5.5 containing 2 mM of each $CaCl_2$, $MgCl_2$, and $MnCl_2$). The oligosaccharides were then eluted with buffer B containing 100 mM $\alpha$-methylmannoside. The oligosaccharides eluted from ConA column were further purified and characterized on a calibrated Bio-gel P-4 column (1.5×200 cm, (−) 400 mesh). The purified oligosaccharides having $Glc_3Man_9GlcNAc$ structure were used as substrate in these studies. Test compounds were dissolved in $H_2O$ or DMSO as appropriate and usually 0.02 to 100 μg/ml concentration of the compound was added to the enzyme before starting the reaction with the radioactive substrate. DMSO controls were run for each experiment, if DMSO was used to dissolve the compounds. ConA-sepharose was washed first with buffer A, then with buffer B as described above, and resuspended in buffer B (gel: buffer, 1:1) before use. The enzymatic assays were performed in a 96 well microplate in a total volume of 100 μl which contained 5000 CPM of [$^3$H]G$_3$M$_9$N substrate, 100 mM potassium phosphate buffer pH 6.8 and purified α-glucosidase I. The reaction mixture was incubated at 37° C. for one hour for each experiment and the reaction stopped by adding 25 μl of glacial acetic acid. To the mixture, 175 μl of concanavalin A-sepharose in buffer B (1:1) was added and microplate was spun at 500×g for 5 minutes. A 150 μl aliquot of supernatant was removed and counted. Using this procedure the results of Table 1 were obtained.

TABLE 1
INHIBITORY ACTIVITY OF
VARIOUS COMPOUNDS OF FORMULA I
AGAINST PURIFIED α-GLUCOSIDASE I

Pig Kidney

[Structure 1: cyclohexane ring with OH, HO, CH$_2$OH, HO, NHCH$_3$, OH substituents] — 2 mM

[Structure 2: cyclohexane ring with OH, HO, CH$_2$OH, HO, NHCH$_3$, OH substituents] — 0.5 mM The derivatives of this invention can be used to treat a number of diseases and conditions associated with Glucosidase I mediated glycoprotein processing such as tumor metastasis and vital infections caused by glycoprotein coated viruses including murine leukemia virus, feline leukemia virus, cytomegalovirus (CMV), avian sarcoma virus, human immunodeficiency virus (HIV), HTLV-I, and HTLV-II. Those experienced in this field are readily aware of the circumstances requiring antiviral or antimetastatic therapy, as well as other circumstances requiring inhibition of Glucosidase I. The term "patient" used herein is taken to mean mammals such as primates, including humans, sheep, horses, cattle, pigs, dogs, cats, rats and mice.

The amount of the formula I derivative of this invention to be administered can vary widely according to the particular dosage unit employed, the period of treatment, the age and sex of the patient treated, the nature and extent of the disorder treated, and the particular derivative selected. Moreover the formula I compound can be used in conjunction with other agents known to be useful in the treatment of vital diseases and tumor metastasis. The antiviral, antimetastatic, and/or Glucosidase I inhibitory derivative of formula I to be administered will generally range from about 15 mg/kg to 500 mg/kg. A unit dosage may contain from 25 to 500 mg of the formula I derivative, and can be taken one or more times per day. The derivative can be administered with a pharmaceutical carrier using conventional dosage unit forms either orally or parenterally. More specifically, the present compounds would be administered to humans in single unit doses containing 35 mg to 350 mg of active ingredient with the material being administered three times a day at mealtime.

In practicing the method of this invention, the active ingredient is preferably incorporated in a composition comprising a pharmaceutical carrier and from about 5 to about 90 percent by weight of a compound of the invention or a pharmaceutically-acceptable salt thereof. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, elixirs, syrups, emulsions, dispersions and wettable and effervescent powders, and can contain suitable excipients known to be useful in the preparation of the particular type of composition desired.

The preferred route of administration is oral administration. For oral administration the formula I compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptable surfactant, suspending agent, or emulsifying agent.

The formula I compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as polyethylene glycol 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically acceptable adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl beta-aminopropionates, and 2-alkylimidazoline quarternary ammonium salts, as well as mixtures. The parenteral compositions of this invention will typically contain from about 0.5 to about 25% by weight of the formula I compound in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The following examples are presented to illustrate the present invention. However, they should not be construed as limiting it in any way.

EXAMPLE 1

6,7-Dideoxy-2,3,4,5-tetrakis-)-(phenylmethyl)-D-gulo/ido-hept-6-enose, Cyclic 1,3-Propanediyl Mercaptals (3a)

Scheme I:

To a stirred solution of 4.45 g (37.0 mmol) of 1,3-dithiane in 100 ml dry THF at −25° to −30° C. under nitrogen was added 23.2 mL (37 mmol) of 1.6M n-BuLi/hexane. After 1 h a solution of 11.87 g (28.50 mmol) of freshly prepared crude aldehyde 2, prepared from bromide 1 according to the procedure of Bernet and Vasella (Bernet, B.; Vasella, A. *Helv. Chim. Acta:* 62 1979 (1990)), in 20 mL dry THF (+2×3 mL rinses) was added. After 2 h (the bath temperature rose to 5° C.) the reaction mixture was poured into aqueous NH$_4$Cl and extracted twice with ether. The combined extracts were washed with+brine, dried (MgSO$_4$), and concentrated in vacuo. The residue was dissolved in 30 mL dry DMF and the resulting solution (+2×2 mL DMF rinses) was added to a vigorously stirred suspension of NaH [1.52 g (38.0 mmol) of 60% dispersion which was first washed 3× with pentane] in 30 mL dry DMF at 0° C. Benzyl bromide (3.56 mL, 29.9 mmol) was then added dropwise. The reaction mixture was allowed to warm to 25° C. overnight (the reaction is complete in less than 1 h) before being quenched with aqueous NH$_4$Cl. The mixture was diluted with water and extracted twice with ether. The extracts were washed twice with water, brine, and dried (MgSO$_4$). Concentration in vacuo and flash chromatography of the residue eluting with 10% EtOAc in cyclohexane gave 12.00 g (67%) of 3a as an orange oil. A portion was resubjected to chromatography eluting with 5% EtOAc in cyclohexane to obtain the analytical sample as a pale straw-colored oil: IR (neat) $v_{max}$ 3080, 3050, 3020, 2920, 2880, 2850, 1700, 1493, 1450, 1085, 1065, 1025, 733, 695 cm$^{-1}$; $^1$H NMR (CDCl$_3$) δ7.4–7.2 (m, 20 H), 5.92–5.77 (m, 1 H), 5.32–5.1 (m, 2 H), 5.01 (d, <1 H), 4.88–4.5 (m, <7 H), 4.4–4.28 (m, 2 H), 4.18–3.63 (m, 4 H), 2.86–2.57 (m, 4 H), 2.08–1.76 (m, 2 H); mass spectrum, m/z 655 (M$^+$+29), 627 (M$^+$+1), 519, 197, 181, 119, 107, 91 (100). Anal. Calcd for C$_{38}$H$_{42}$O$_4$S$_2$: C, 72.81; H, 6.75; S, 10.23. Found: C, 73.09; H, 6.78, S, 10.09.

EXAMPLE 2

6,7-Dideoxy-2-[(4-methoxyphenyl)methoxy]-3,4,5-tris-O-(phenylmethyl)-D-gulo/ido-hept-6-enose, Cyclic 1,3-Propanediyl Mercaptals (3b)

Scheme I:

An identical procedure utilizing 25.05 g (47.5 mmol) of bromide 1 and subsequently 6.75 mL (49.8 mmol) of 4-methoxybenzyl chloride gave 23.75 g (76%) of dithianes 3b contaminated by 7% of methyl-6-deoxy-2,3,4-tris(phenylmethoxy)-α-D-glucopyranoside. A portion of the material was rechromatographed eluting with 4, then 5% EtOAc in cyclohexane to give the analytical sample: IR (neat) $v_{max}$ 2934, 2898, 1514, 1454, 1248, 1086, 1068, 1028, 752, 736, 698 cm$^{-1}$; $^1$H NMR (CDCl$_3$) δ7.38–7.22, (m, 17 H), 6.83 (d, 1 H, J=4.6 Hz), 6.80 (d, 1 H, J=4.6 Hz), 5.91–5.77 (m, 1 H), 5.32–5.11 (m, 2 H), 4.95–4.67 (m, 4 H), 4.64–4.56 (m, 2 H), 4.48 (d, 0.5 H, J=10.7 Hz), 4.40–4.27 (m, 1.5 H), 4.17–3.79 (m, 4.5 H), 3.78 and 3.77 (2s, 3 H), 3.71 (t, 0.5 H, J=5.3 Hz), 2.86–2.56 (m, 4 H), 2.09–1.78 (m, 2 H); mass spectrum, m/z 697 (M$^+$+41), 685 (M$^+$+29), 657 (M$^+$+1), 227, 121, 107 (100), 91. Anal. Calcd for C$_{39}$H$_{44}$O$_5$S$_2$: C, 71.31; H, 6.75; S, 9.76. Found: C, 71.21; H, 6.84; S, 9.55.

EXAMPLE 3

6,7-Dideoxy-2,3,4,5-tetrakis-O-(phenylmethyl)-D-gulo-hept-6-enose (4a) and 6,7-Dideoxy-2,3,4,5-tetrakis-O-(phenylmethyl)-D-ido-hept-6-enose (5a)

Scheme I:

A solution of 5.661 g (9.03 mmol) of dithianes 3a in 11 mL CH$_3$CN (+2×3 mL CH$_3$CN rinses) was added rapidly to a vigorously stirred solution of 3.566 g (26.7 mmol) of N-chlorosuccinimide (NCS) and 5.084 g (29.9 mmol) of AgNO$_3$ in 165 mL aqueous 80% CH$_3$CN. AgCl separated immediately. The mixture was stirred for 45 min. Saturated aqueous Na$_2$S$_2$O$_3$, Na$_2$CO$_3$, and NaCl solutions were added and after 10–15 min the mixture was diluted with EtOAc/H$_2$O and filtered through filter aid. The organic layer was separated from the filtrate and the aqueous layer was extracted with additional EtOAc. The combined extracts were washed with dilute aqueous NaCl, saturated aqueous NaCl, and dried (MgSO$_4$). The solvent was removed in vacuo and the residue purified by flash chromatography eluting with first 10%, then 15% EtOAc in cyclohexane to give 0.510 g (10.5%) of 4a and 1.954 g (40%) of the more polar 5a as colorless oils.

For 4a: IR (neat) $\nu_{max}$ 3060, 3030, 2865, 1732, 1499, 1458, 1090, 1070, 1032, 740, 700 cm$^{-1}$; $^1$H NMR (CDCl$_3$) $\delta$9.69 (d, 1 H, J=1.3 Hz), 7.33–7.22 (m, 20 H), 5.89–5.77 (m, 1 H), 5.30 (bs, 1 H), 5.26 (m, 1 H), 4.76 (d, 1 H, J=11.3 Hz), 4.71 (d, 1 H, J=11.3 Hz), 4.64 (d, 1 H, J=11.3 Hz), 4.60 (d, 1 H, J=11.7 Hz), 4.56 (d, 1 H, J=11.6 Hz), 4.55 (d, 1 H, J=11.3 Hz), 4.33 (d, 1 H, J=11.7 Hz), 4.31 (d, 1 H, J=11.6 Hz), 4.14 (dd, 1 H, J=7.3, 5.8 Hz), 4.05–3.99 (m, 2 H), 3.73 (t, 1 H, J=5.5 Hz); $^{13}$ NMR (CDCl$_3$) $\delta$201.57, 138.22, 138.13, 138.01. 137.38, 135.00, 128.42, 128.31, 128.27, 128.22, 127.98, 127.91, 127.88, 127.80, 127.64, 127.58, 127.55, 119.19, 84.24, 81.31, 81.02, 80.70, 75.05, 73.88, 72.46, 70.49; mass spectrum, m/z 537 (M$^+$+1), 429, 337, 181, 107, 91 (100); exact mass calcd for C$_{35}$H$_{37}$O$_5$ 537.2641, found 537.2654.

For 5a: IR (neat) $\nu_{max}$ 3055, 3025, 2860, 1725, 1493, 1450, 1110, 1085, 1065, 1025, 733, 695 cm$^{-1}$; $^1$H NMR (CDCl$_3$) $\delta$9.59 (s, 1 H), 7.34–7.20 (m, 20 H), 5.84–5.71 (m, 1 H), 5.27 (dd, 1 H, J=10.5, 1.6 Hz), 5.18 (dd, 1 H, J=17.3, 1.2 Hz), 4.73 (d, 1 H, J=12.0 Hz), 4.68 (d, 1 H, J=10.8 Hz), 4.63 (d, 1 H, J=12 Hz), 4.59 (d, 1 H, J=11 Hz), 4.58 (d, 1 H, J=11.8 Hz), 4.52 (d, 1 H, J=11.5 Hz), 4.30 (d, 1 H, J=12.0 Hz), 4.24 (d, 1 H, J=11.7 Hz), 4.01 (t, 1 H, J=4.6 Hz), 3.88 (dd, 1 H, J=7.1, 5.9 Hz), 3.79 (t, 1 H, J=5.2 Hz), 3.67 (d, 1 H, J=4.6 Hz); $^{13}$H NMR (CDCl$_3$) $\delta$200.82, 138.08, 137.70, 137.30, 135.21, 128.48, 128.38, 128.36, 128.31, 128.23, 128.16, 128.05, 127.90, 127.66, 127.51, 119.12, 81.07, 80.40, 80.22, 79.77, 74.68, 74.15, 72.96, 70.42; mass spectrum, m/z 537 (M$^+$+1), 429, 321, 231, 181, 91 (100); exact mass calcd for C$_{35}$H$_{37}$O$_5$ 537.2641; found 537.2598.

EXAMPLE 3a 6,7-Dideoxy-2-[(4-methoxyphenyl)methoxy]-3,4,5-tris-O-(phenylmethyl)-D-gulo-hept-6-enose (4b) and 6,7-Dideoxy-2-[(4-methoxyphenyl)methoxy]-3,4,5-tris-O-(phenylmethyl)-D-ido-hept-6-enose (5b)

Scheme I:

Modification of the above procedure used in the preparation of 4a/5a, employing 1.61 eq of NCS and 2.01 eq AgClO$_4$ in aqueous 90% acetone, gave a 67% yield of 4b/5b after flash chromatography of the crude product through a very short column of silica gel eluting with 15% ethyl acetate in cyclohexane. Careful rechromatography eluting with 10–12.5% ethyl acetate in cyclohexane gave 4b followed by 5b in a 2:1 ratio. However, the mixture was normally used in the cycloaddition reactions due to the lability of the aldehydes.

For 4b: $^1$H NMR (CDCl$_3$) $\delta$9.68 (s, 1 H), 7.3–7. 22 (m, 15 H), 7.18 (d, 2 H, J=8.7 Hz), 6.81 (d, 2 J=8.7 Hz), 5.89–5.77 (m, 1 H), 5.27 (d, 1H, J=15.9 Hz), 5.26 ( d, 1 H, J=11.8 Hz), 4.75 (d, 1 H, J=11.3 Hz), 4.70 (d, 1 H, J=11.3 Hz), 4.63 (d, 1 H, J=11.3 Hz), 4.54 (d, H, J=1 1.5 Hz), 4.54 (d, 1 H, J=11.2 Hz), 4.52 (d, 1 H, J=11.5 Hz), 4.29 (d, 1 H, J=11.6 Hz), 4.28 (d, 1 H, J=11.5 Hz), 4.14 (dd, 1 H, J=7.3, 6.1 Hz), 4.04–4.01 (m, 2 H), 3.73 (t, 1 J=5.3 Hz), 3.68 (s, 3 H).

For 5b: $^1$H NMR (CDCl$_3$) $\delta$9.58 (s, 1 H), 7.32–7.20 (m, 15 7.16 (d, 2 H, J=8.7 Hz), 6.85 (d, 2 H, J=8.6 Hz), 5.84–5.72 (m, 1 H), 5.28 (dd, 1 H, J=10.4 and 1.8 Hz), 5.18 (ddd, 1 H, J=17.3, 1.8, and 0.7 Hz), 4.68 (d, 1 H, J=10.9 Hz), 4.64 (d, 1 H, J=12.0 Hz), 4.63 (d, 1 H, J=11.5 Hz), 4.60 (d, 1 H, J=10.7 Hz), 4.58 (d, 1 H, J=11.8 Hz), 4.52 (d, 1 H, J=11.5 Hz), 4.26 (d, H, J=11.8 Hz), 4.25 (d, 1 H, J=11.8 Hz), 4.00 (t, 1 H, J=4.7 Hz), 3.86 (dd, 1 H, J=7.5 and 5.7 Hz ), 3.81 (S, 3 H), 3.81–3.75 (m, 1 H), 3.66 (d, 1 H, J=4.6 Hz ).

EXAMPLE 4

(−)-(3a$\alpha$,4$\beta$,5$\alpha$,6$\beta$,7$\alpha$,7a$\alpha$)-Octahydro-1-methyl-4,5,6,7-tetrakis(phenylmethoxy)-2,1-benzisoxazole (6a) and (3a$\alpha$,4$\alpha$,5$\beta$,6$\alpha$,7$\beta$,7a$\beta$)-Octahydro-1-methyl-4,5,6,7-tetrakis(phenylmethoxy)-2,1-benzisoxazole (7a)

Scheme I:

A solution (suspension) of CH$_3$NHOH (NaCl) in 10 mL CH$_3$OH [prepared from 230 mg (4.26 mmol) of CH$_3$ONa and 362 mg (4.33 mmol) of CH$_3$NHOH.HCl] was added to a stirred solution of 1.904 g (3.55 mmol) of 5a in 40 mL CH$_3$OH and the resulting solution was heated at reflux under nitrogen for 4 h, then allowed to stir at 25° C. for 2.5 days. The solution was partially concentrated in vacuo. The residue was diluted with water and extracted twice with EtOAc/cyclohexane. The combined extracts were washed with water, brine, and dried (MgSO$_4$). Concentration in vacuo and flash chromatography of the residue eluting with 23% EtOAc in cyclohexane gave 1.21 g (60%) of cis isomer 6a and 0.321 g (16%) of the more polar trans isomer 7a as white solids. Recrystallization of each from ether/pentane gave 6a as fine white needle s and 7a as matted white crystals.

For 6a: mp 58.5°–61° C.; IR (KBr) $\nu_{max}$ 2882, 1496, 1454, 1358, 1114, 1086, 1070, 736, 698 cm$^{-1}$; $^1$H NMR (CDCl$_3$) $\delta$7.33–7.25 (m, 20 H), 4.93 (d, 1 H, J=11 Hz), 4.93 (d, 1 H, J=10.9 Hz), 4.83 (d partially obscured by peak at $\delta$4.815, 1 H), 4.815 (s, 2 H), 4.78 (s, 2 H), 4.71 (d, 1 H, J=11.8 Hz), 4.62 (d, 1 H, J=11.8 Hz), 4.15 (dd, 1 H, J=9.0, 8.7 Hz), 3.90 (t, 1H, J=8.7 Hz), 3.82–3.69 (m, 3 H), 3.48 (dd, 1 H, J=9.0, 8.0 Hz) , 3.32 (m, 1 H, J=9.0, 8.7, 8.3 Hz), 2.99 (t, H, J=8.3 Hz), 2.68 (s, 3H); $^{13}$C NMR (CDCl$_3$) $\delta$138.83, 138.54, 138.36, 138.14, 128.33, 128.26, 128.23, 128.19, 128.10, 128.02, 127.99, 127.86, 127.79, 127.72, 127.69, 127.62, 127.55, 127.44, 127.37, 83.14, 81.10, 77.62, 75.12, 75.04, 74.92, 72.69, 70.04, 67.02, 44.98, 42.34; mass spectrum, m/z 594 (M$^+$+29), 566 (M$^+$+I), 476, 107, 91 (100); [$\alpha$]$_D^{25}$ −13 3° (c 1.1, CHCl$_3$).

Anal. Calcd for C$_{36}$H$_{39}$NO$_5$; C,76.43; H, 6.95; N, 2.48. Found: C, 76.48; H, 7.01; N, 2.36.

For 7a: mp 85°–87.5° C.; IR (KBr) $\nu_{max}$ 2910, 2854, 1496, 1454, 1356, 1158, 1142, 1130, 1086, 1068, 1050, 736, 696 cm$^{-1}$; $^1$H NMR (CDCl$_3$) $\delta$7.33–7.24 (m, 20 H), 4. 93–4.84 (m, 4 H), 4.84 (d, 1 H, J=10.9 Hz), 4.72 (d, 1 H, J=11.5 Hz), 4.705 (d, 1 H, J=10.9 Hz), 4.55 (d, 1 H, J=11 .5 Hz), 4.02 (t, 1 H, J=6.9 Hz), 3.77–3.65 (m, 3 H), 3.5 9 (dd, 1 H, J=10.5, 7.1 Hz), 3.56 (dd, 1 H, J=10.9, 8.5 Hz), 2.80 (s, 3 H), 2.57 (dq, 1 H, J=7.0, 10.7 Hz), 2.37 (dd, 1 H, J=11.1, 9.4 Hz); $^{13}$C NMR (CDCl$_3$) $\delta$138.37, 138.31, 137.94, 137.88, 128.47, 128.40, 127.96, 127.92, 127.83, 127.75, 127.68, 127.64, 87.02, 85.93, 82.73, 79.77, 76.10, 75–96, 74.60, 73.87, 70.58, 67.80, 50.41, 47.60; mass spectrum, m/z 594 (M$^+$+29), 566 (M$^+$+1), 476, 107, 91 (100). Anal. Calcd for C$_{36}$H$_{39}$NO$_5$: C, 76.43; H, 6.95; N, 2.48. Found: C, 76.35; H, 6.99; N, 2.31.

EXAMPLE 5

(−)-(3aα,4β,5α,6β,7α,7aα)-Octahydro-7-[(4-methoxyphenyl)methoxy]-1-methyl-4,5,6-tris(phenylmethoxy)-2,1-benzisoxazole (6b) and
(−)-(3aα,4α,5β,6α,7β,7aβ)-Octahydro-7-[(4-methoxyphenyl)methoxy]-1-methyl-4,5,6-tris(phenylmethoxy)-2,1-benzisoxazole (7b)

Scheme II:

Using a similar procedure in which the reactants were heated at reflux for 22 h, cis isomer 6b and the more polar trans isomer 7b were obtained in yields of 69 and 17% respectively after flash chromatography eluting with 25% EtOAc in cyclohexane. The cis isomer was obtained as a pale straw-colored oil which partially crystallized upon standing; trituration with pentane gave a white solid. The trans isomer was obtained as matted white needles after recrystallization from ether/pentane.

For 6b: mp 59°–61° C.; IR (neat) $\nu_{max}$ 3030, 2952, 2884, 1612, 1514, 1496, 1454, 1358, 1302, 1248, 1210, 1172, 1156, 1112, 1070, 1030, 822, 736, 698 cm$^{-1}$; $^1$H NMR (CDCl$_3$) δ7.38–7.22 (m, 17 H), 6.83 (d, 2 H, J=7.4 Hz), 4.9–4.74 (m, 6 H), 4.72 (d, 1 H, J=12 Hz), 4.63 (d, 1 H, J=12 Hz), 4.16 (t, 1 H, J=8.7 Hz), 3.90 (t, 1 H, J=8.5 Hz), 3.82–3.67 (m, 3 H), 3.76 (s, 3 H), 3.46 (t, 1 H, J=8.4 Hz), 3.33 (m, 1 H), 2.98 (t, 1 H, J=7.9 Hz), 2.69 (s, 3 H); mass spectrum, m/z 636 (M$^+$+41), 624 (M$^+$+29), 596 (M$^+$+1), 488, 121, 92, 91 (100); $[\alpha]_D^{25}$ −22.7° (c 1.00, CHCl$_3$). Anal. Calcd for C$_{37}$H$_{41}$NO$_6$: C, 74.60; H, 6.94; N, 2.35. Found: C, 74.72; H, 6.95; N, 2.19.

For 7b: mp 77°–79° C.; IR (KBr) $\nu_{max}$ 2910, 1514, 1354, 1250, 1144, 1130, 1062, 1044, 990, 754, 734, 696 cm$^{-1}$; $^1$H NMR (CDCl$_3$) δ7.37–7.23 (m, 15 H), 7.20 (d, 2 H, J=8.5 Hz), 6.82 (d, 2 H, J=8.5 Hz), 4.91 (s, 2 H), 4.90 (s, 2 H), 4.78 (d, 1 H, J=10.4 Hz), 4.70 (d, 1 H, J=11.5 Hz), 4.64 (d, 1 H, J=10.4 Hz), 4.54 (d, 1 H, J=11.5 Hz), 4.02 (t, 1 H, J=6.7 Hz), 3.77–3.50 (m, 5 H), 3.71 (s, 3 H), 2.82 (s, 3 H), 2.64–2.50 (m, 1 H), 2.35 (dd, 1 H, J=11, 9.6 Hz); mass spectrum, m/z 624 (M$^+$+29), 596 (M$^+$+1), 137, 121, 107, 92, 91 (100); $[\alpha]_D^{25}$ −12.0° (c 0.61, CHCl$_3$).

Anal. Calcd for C$_{37}$H$_{41}$NO$_6$: C, 74.60; H, 6.94; N, 2.35. Found: C, 74.50; H, 7.01; N, 2.25.

EXAMPLE 6

1,2-Dideoxy-2-(hydroxymethyl)-1-(methylamino)-myo-inositol Hydrochloride (8)

Scheme II:

Hydrogenation of a solution of 826 mg (1.46 mmol) of 6a in 25 mL HOAc containing 192 mg Pd black as catalyst in a Parr hydrogenation apparatus for 2 days gave after removal of solvent, addition of dilute HCl, and concentration in vacuo a crystalline solid. Recrystallization from CH$_3$CN/CH$_3$OH gave 269 mg (76%) of 8 as pale amber crystalline granules: mp 201° dec; IR (KBr) $\nu_{max}$ 3412, 3298, 3196, 3122, 1616, 1466, 1104, 1080, 1044, 1034, 1022, 1014, 946 cm$^{-1}$; $^1$H NMR (DMSO-d$_6$, D$_2$O) δ3.82–3.76 (m obscured by HOD peak), 3.66 (dd, 1 H, J=10.9, 8.9 Hz), 3.60 (dd, 1 H, J=11.0, 9.4 Hz), 3.38 (dd, 1 H, J=9.9, 5.1 Hz), 3.14 (dd, 1 H, J=9.6, 9.1 Hz), 2.98 (t, 1 H, J=9.1 Hz), 2.96 (dd, 1 H, J=11.1, 4.4 Hz), 2.63 (s, 3 H), 2.47–2.39 (m, 1 H, J=9.0, 4.4 Hz); $^{13}$C NMR (DMSO-d$_6$) δ76.29, 73.10, 70.41, 69.76, 60.63, 55.91, 40.30, 31.99; mass spectrum, m/z 248 (M$^+$+41), 236 (M$^+$+29), 208 (M$^+$+1, 100), 190, 116.

Anal. Calcd for C$_8$H$_{17}$NO$_5$.HCl: C, 39.43; H, 7.45; N, 5.75. Found: C, 39.62; H, 7.69; N, 5.59.

EXAMPLE 7

1,2-Dideoxy-2-(hydroxymethyl)-1-(methylamino)-scyllo-inositol (9)

Scheme II:

Similar hydrogenation of a solution of 322 mg (0.569 mmol) of 7a in 16 mL aqueous 80% HOAc containing 101 mg Pd black for 3 days gave, after flash chromatography eluting with 3:1:2 CH$_3$OH: conc NH$_4$OH:CH$_2$Cl$_2$ and lyophilization from water, 108 mg (92%) of 9 as a hygroscopic faint beige foam: $^1$H NMR (D$_2$O) δ3.89 (dd, 1 H, J=11.6, 3.9 Hz), 3.84 (dd, 1 H, J=11.6, 3.1 Hz), 3.51 (dd, 1 H, J=9.9, 9.2 Hz), 3.44–3.23 (m, 3 H), 2.65 (dd, 1 H, J=11.3, 10.5 Hz), 2.39 (s, 3 H), 1.65 (tt, 1 H, J=10.9, 3.5 Hz ); $^{13}$C NMR (D$_2$O) δ79.47, 78.12, 75.37, 73.55, 61.96, 61.16, 45.81, 33.58; mass spectrum, m/z 248 (M$^+$+41), 236 (M$^+$+29), 208 (M$^+$+1, 100), 190; exact mass calcd for C$_8$H$_{18}$NO$_5$ 208.1185, found 208.1188.

EXAMPLE 8

(+)9b
3aα,4α,5β,6α,7α)-3,3a,4,5,6,7-Hexahydro-4,5,6,7-tetrakis((phenylmethoxy)-2,1,-benzisoxazole (10a)

Scheme III:

A solution (suspension) of NH$_2$OH (NaCl) in 2 mL CH$_3$OH [prepared from 64 mg (1.2 mmol) of CH$_3$ONa and 86 mg (1.2 mmol) of NH$_2$OH.HCl] was added to a stirred solution of 403 mg (0.751 mmol) of 4a in 8 mL CH$_3$OH under nitrogen. After 18 h the solution was concentrated in vacuo and the residue partitioned between EtOAc/cyclohexane and water. The organic layer was washed with water then concentrated in vacuo. The residue was dissolved in 10 mL CH$_2$Cl$_2$ and the solution cooled to 0° C. To the vigorously stirred solution was added 1.3 mL of commercial bleach. The reaction mixture was allowed to stir at 25° C. for 20 h, after which time an additional 0.7 mL of bleach was added. After 24 h more the mixture was diluted with water and extracted with EtOAc/cyclohexane. The extracts were washed with water and then concentrated in vacuo. Flash chromatography of the reisdue (420 mg) eluting with 17.5% EtOAc in cyclohexane gave 337 mg (82%) of white crystals. Recrystallization from ether/pentane gave 10a as white granules: mp 90.5°–93° C.; IR (KBr) $\nu_{max}$ 3032, 2924, 2872, 1496, 1454, 1358, 1098, 1074, 1046, 1028, 854, 736, 696 cm$^{-1}$; $^1$H NMR (CDCl$_3$) δ7.41–7.21 (m, 20 H), 5.03 (d, 1 H, J=10.7 Hz), 4.83 (d, 1 H, J=11.8 Hz), 4.82 (d, 1 H, J=10.4 Hz), 4.63 (d, 2 H, J=12.4 Hz), 4.58–4.56 (m, 2 H), 4.51 (d, 1 H, J=3.5 Hz), 4.46 (d, 1 H, J=12.4 Hz), 4.35 (dd, 1 H, J=10.7, 8.5 Hz), 4.15 (t, 1 H, J=9.3 Hz), 3.815 (t, 1 H, J=8.5 Hz), 3.52 (td, 1 H, J=10.4, 8.6 Hz), 3.445 (dd, 1 H, J=9.8, 3.5 Hz), 3.35 (dd, 1 H, J=9.8, 9.0 Hz); $^{13}$C NMR (CDCl$_3$) δ154.66, 138.54, 137.99, 137.65, 136.89, 128.48, 128.40, 128.36, 128.32, 128.15, 127.99, 127.83, 127.78, 127.60, 82.19, 81.93, 80.85, 76.02, 74.41, 73.35, 72.39, 70.92, 68.85, 50.83; mass spectrum, m/z 590 (M$^+$+41), 578 (M$^+$+29), 550 (M$^+$+1, 100), 107, 91; $[\alpha]_D^{25}$ +47.7° (c 0.93, CHCl$_3$). Anal. Calcd for C$_{35}$H$_{35}$NO$_5$: C, 76.48; H, 6.42; N, 2.55. Found: C, 76.60,; H, 6.39; N, 2.44.

EXAMPLE 9

(+)-3a$\alpha$,4$\alpha$,5$\beta$,6$\alpha$,7$\alpha$)-3,3a,4,5,6,7-Hexahydro-7-[(4-methoxyphenyl)-methoxy]-4,5,6-tris(phenylmethoxy)-2,1-benzisoxazole (10b)

Scheme III:

Using a similar procedure, 10b was obtained in 76% yield after purification by flash chromatography eluting with 17% EtOAc in cyclohexane. Recrystallization from cyclohexane gave 10b as matted white crystals: mp 118°–120° C.; IR (KBr) $\nu_{max}$ 2932, 2884, 1512, 1454, 1244, 1098, 1076, 1028, 858, 734, 696 cm$^{-1}$; $^1$H NMR (CDCl$_3$) $\delta$7.39–7.23 (m, 17 H), 6.88 (d, 2 H, J=8.6 Hz), 5.03 (d, 1 H, J=10.6 Hz), 4.84 (d, 1 H, J=11.5 Hz), 4.82 (d, 1 H, J=10.6 Hz), 4.60 (d, 1 H, J=11.5 Hz), 4.59 (d, 1 H, J=12.1 Hz), 4.55 (s, 2 H), 4.50 (d, 1 H, J=3.5 Hz), 4.40 (d, 1 H, J=12.1 Hz), 4.36 (dd, 1 H, J=10.7, 8.5 Hz), 4.13 (dd, 1 H, J=9.5, 9.0 Hz), 3.82 (t, 1 H, J=8.5 Hz), 3.81 (s, 3 H), 3.57–3.46 (m, 1 H), 3.44 (dd, 1 H, J=9.8, 3.5 Hz), 3.34 (dd, 1 H, J=9.8, 9.0 Hz); $^{13}$C NMR (CDCl$_3$) $\delta$159.76, 155.08, 138.78, 138.23, 137.88, 130.48, 129.04, 128.69, 128.55, 128.35, 128.20, 128.04, 127.97, 127.82, 113.92, 82.26, 81.92, 80.79, 76.04, 74.43, 73.32, 72.25, 70.45, 68.17, 55.16, 50.76; mass spectrum, m/z 620 (M$^+$+41), 608 (M$^+$+29), 580 (M$^+$+1), 137, 121, 107, 91 (100), 79; $[\alpha]_D^{25}$ +55.1° (c 1.08, CHCl$_3$). Anal. Calcd for C$_{36}$H$_{37}$NO$_6$: C, 74.59; H, 6.43; N, 2.42. Found: C, 74.55; H, 6.39; N, 2.33.

EXAMPLE 10

(−)-3a$\alpha$,4$\alpha$,5$\beta$,6$\alpha$,7$\beta$)-3,3a,4,5,6,7-Hexahydro-4,5,6,7-tetrakis(phenylmethoxy)-2,1-benzisoxazole (14a)

Scheme IV:

Using a similar procedure, 14a was obtained in 46% yield after recrystallization of the crude product mixture from hexane/EtOAc. An additional 6% of 14a was isolated after flash chromatography of the mother liquor eluting with 13% EtOAc in cyclohexane: mp 117.5°–119.5° C.; IR (KBr) $\nu_{max}$ 3032, 2890, 2872, 1498, 1454, 1356, 1132, 1092, 1070, 738, 698 cm$^{-1}$; $^1$H NMR (CDCl$_3$) $\delta$7.41–7.23 (m, 20 H), 5.04 (d, 1 H, J=11.5 Hz), 4.98 (d, 1 H, J=10.7 Hz), 4.94 (d, 1 H, J=10.7 Hz), 4.84 (d, 1 H, J=11.5 Hz), 4.83 (d, 1 H, J=10.7 Hz), 4.82 (d, 1 H, J=10.7 Hz), 4.67 (d, 1 H, J=11.5 Hz), 4.60 (d, 1 H, J=11.5 Hz), 4.44 (dd, 1 H, J=10.3, 8.5 Hz), 4.36 (m, 1 H), 3.89 (t, 1 H, J=8.5 Hz), 3.72–3.62 (m, 2 H), 3.47–3.40 (m, 1 H), 3.36–3.26 (m, 1 H); $^{13}$C NMR (CDCl$_3$) $\delta$154.47, 138.23, 138.17, 137.82, 137.56, 128.55, 128.40, 128.38, 128.34, 128.11, 128.06, 128.05, 128.01, 127.86, 127.83, 127.74, 127.73, 127.70, 84.90, 83.69, 81.16, 77.38, 76.16, 76.05, 74.63, 73.19, 72.77, 52.44; mass spectrum, m/z 590 (M$^+$+41), 578 (M$^+$+29), 550 (M$^+$+1), 107, 91 (100); $[\alpha]_D^{25}$ −35.6° (c 0.95, CHCl$_3$). Anal. Calcd for C$_{35}$H$_{35}$NO$_5$: C, 76.48; H, 6.42; N, 2.55. Found: C, 76.44; H, 6.47; N, 2.46.

EXAMPLE 11

(−)-3a$\alpha$,4$\alpha$,5$\beta$,6$\alpha$,7$\beta$)-3,3a,4,5,6,7-Hexahydro-7-[(4-methoxyphenyl)methoxy]-4,5,6-tris(phenylmethoxy-2,1-benzisoxazole (14b)

Scheme IV:

Using a similar procedure in which a 3:1 mixture of aldehydes 5b and 4b were utilized as starting materials, 18% of 10b and 35% of 14b were isolated after flash chromatography eluting with 13, then 15% EtOAc in cyclohexane.

For 14b: mp 133°–135° C.; IR (KBr) $\nu_{max}$ 2881, 1511, 1247, 1158, 1132, 1091, 1070, 737, 699 cm$^{-1}$; $^1$H NMR (CDCl$_3$) $\delta$7.35–7.22 (m, 17 H), 6.82 (d, 2 H, J=8.7 Hz), 4.96 (d, 1 H, J=10.9 Hz), 4.96 (d, 1 H, J=10.6 Hz), 4.93 (d, 1 H, J=10.2 Hz), 4.82 (d, 2 H, J=10.4 Hz), 4.80 (d, 1 H, J=10.8 Hz), 4.60 (d, 1 H, J=11.3 Hz), 4.58 (d, 1 H, J=11.5 Hz), 4.42 (dd, 1 H, J=10.4, 8.5 Hz), 4.33 (m, 1 H), 3.89 (t, 1 H, J=8.5 Hz), 3.73 (s, 3 H), 3.71–3.60 (m, 2 H), 3.47–3.39 (m, 1 H), 3.33–3.22 (m, 1 H); $^{13}$C NMR (CDCl$_3$) $\delta$159.58, 154.87, 138.43, 138.31, 137.97, 129.96, 129.86, 129.78, 128.66, 128.52, 128.45, 128.23, 128.16, 128.10, 127.99, 127.85, 127.80, 113.83, 84.80, 83.58, 81.06, 76.92, 76.03, 75.96, 74.51, 72.72, 72.64, 55.05, 52.22; mass spectrum, m/z 608 (M$^+$+29), 580 (M$^+$+1), 137, 121 (100), 107, 92, 91; $[\alpha]_D^{25}$ −34.6° (c 1.1, CHCl$_3$). Anal. Calcd for C$_{36}$H$_{37}$NO$_6$: C, 74.59; H, 6.43; N, 2.42. Found: C, 74.79; H, 6.54; N, 2.34.

EXAMPLE 12

(3a$\alpha$,4$\alpha$,5$\beta$,6$\alpha$,7$\alpha$,7a$\beta$)-Octahydro-1-methyl-4,5,6,7,-tetrakis-(phenylmethoxy)-2,1-benzisoxazole (12a)

Scheme III:

To a stirred solution of 773 mg (1.41 mmol) of 10a in 8 mL 99% CH$_3$NO$_2$ under nitrogen was added 237 mg (1.60 mmol) of trimethyloxonium tetrafluoroborate. After 1 h an additional 42 mg (0.28 mmol) of Meerwein's salt was added and the solution was stirred for 2 h. Concentration in vacuo gave 1.007 g of tacky pale amber glass. "An ice cold solution of 114 mg (3.01 mmol) of NaBH$_4$ in 10 mL EtOH was added to 890 mg (1.25 mmol) of the glass with swirling and ice bath cooling. The stirred solution was allowed to warm to 25° C. overnight. The excess NaBH$_4$ was quenched with HOAc and the reaction mixture was diluted with aqueous KOH and extracted with several portions of EtOAc. The combined extracts were washed with brine, dried (MgSO$_4$), and concentrated in vacuo to give 692 mg of a pale yellow oil. This was combined with 196 mg of material from similar reductions and purified by flash chromatography on silica gel eluting with first 17.5%, then 30% EtOAc in cyclohexane to give, along with 320 mg (35%) of 11a, 180 mg (20%) of the more polar 12a as a white solid: $^1$H NMR (C$_6$D$_6$) $\delta$7.49 (d, 2 H, J=7.3 Hz), 7.36 (m, 4 H), 7.24–7.05 (m, 14 H), 4.98 (d, 1 H, J=11 Hz), 4.96 (d, 1 H, J=12 Hz), 4.82 (d, 1 H, J=11.1 Hz), 4.72 (d, 1 H, J=12 Hz), 4.61 (d, 1 H, J=11.9 Hz), 4.49 (d, 1 H, J=11.9 Hz), 4.47 (s, 2 H), 4.22 (dd, 1 H, J=9.2, 8.5 Hz), 4.11 (pseudo t, 1 H, J=3.3 Hz), 3.74 (bs, 1 H), 3.44–3.39 (m, 2 H), 3.305 (dd, 1 H, J=10.2, 8.5 Hz), 3.27 (dd, 1 H, J=9.2, 2.7 Hz), 2.51 (s, 3 H), 1.78 (bd, 1 H, J=9.2 Hz); $^{13}$C NMR (C$_6$D$_6$) $\delta$139.92, 139.26, 139.07, 128.57, 128.38, 128.31, 128.23, 128.11, 127.99, 127.93, 127.86, 127.76, 127.68, 127.42, 84.54, 83.47, 81.12, 75.83, 73.97, 73.24, 72.51, 72.05, 70.90, 68.64, 46.90, 44.71.

EXAMPLE 13

1,6-Dideoxy-6-(hydroxymethyl)-1-(methylamino)-myo-inositol (13)

Scheme III:

Hydrogenation of a solution off 180 mg (0.318 mmol) of 12a in 10 mL of aqueous 80% HOAc containing 54 mg Pd black in a Parr shaker for 3 days gave 54 mg of crude material. Flash chromatography eluting with 3:1:2 $CH_3OH$: conc $NH_4OH$: $CH_2Cl_2$ gave 33 mg of colorless oil which was dissolved in 3 mL aqueous HOAc at 45° C. and treated with Zn dust for 1.5 h. Concentration in vacuo and rechromatography gave 24 mg of 13 as a colorless oil: $^1H$ NMR ($D_2O$) δ4.24 (t, 1 H, J=2.7 Hz), 3.91 (dd, 1 H, J=11.5, 3.0 Hz), 3.83 (dd, 1 H, J=11.5, 5.2 Hz), 3.60 (pseudo t, 1 H, J~9.7 Hz), 3.39 (dd, 1 H, J=10.1, 2.9 Hz), 3.27 (dd, 1 H, J=10.8, 9.2 Hz), 2.78 (dd, 1 H, J=11.6, 2.6 Hz), 2.45 (s, 3 H), 1.77 (m, 1 H); mass spectrum, m/z 248 ($M^+$+41), 236 ($M^+$+29), 208 ($M^+$+1, 100), 190; exact mass calcd for $C_8H_{18}NO_5$ 208.1185, found 208.1187.

EXAMPLE 14

(+)-1-Amino-1,2-dideoxy-2-(hydroxymethyl)-6-[(4-methoxyphenyl)methoxyl]-3,4,5-tris(phenylmethoxy)-scyllo-inositol (15b)

Scheme IV:

A solution/suspension of 632 mg (1.09 mmol) of 14b and 273 mg (4.42 mmol) of $B(OH)_3$ in 45 mL $CH_3OH$ and 3.5 mL water and 0.57 g (wet weight after several washings with water) of Raney nickel (Aldrich) were placed in a Parr hydrogenation apparatus and shaken under a hydrogen atmosphere for 22 h. The mixture was filtered through filter aid and the filtrate (and $CH_3OH$ washings) was concentrated in vacuo. The residue was partitioned abetween EtOAc and water. The organic layer was washed with brine, dried ($MgSO_4$), and concentrated in vacuo to give 597 mg of semi-crystalline material. Recrystallization from cyclohexane/EtOAc gave 166 mg (26%) of 15b as white crystals. A second recrystallization gave the analytical sample: mp 160°–161° C.; IR (KBr) $\nu_{max}$ 3424, 2908, 1514, 1248, 1086, 1068, 1028, 736, 696 cm$^{-1}$; $^1H$ NMR (CDCl$_3$) δ7.35–7.26 (m, 15 H), 7.22 (d, 2 H, J=8 .7 Hz), 6.88 (d, 2 H, J=8.7 Hz), 4.97–4.85 (m, 6 H), 4.5 7 (d, 1 H, J=11.0 Hz), 4.56 (d, 1 H, J=10.9 Hz), 41.02 (dd, 1 H, J=10.8, 3.1 Hz), 3.80 (s, 3 H), 3.66 (dd, 1 H, J=10.9, 7.3 Hz), 3.62 (t, 1 H, J=9.3 Hz), 3.49 (t, 1 H, J=9.3 Hz) , 3.24 (dd, 1 H, J=10.7, 9.2 Hz), 3.11 (t, 1 H, J=9.4 Hz) , 2.54 (dd, 1 H, J=11.1, 9.9 Hz), 2.33 (bs, 3 H), 1.55 (m, 1 H); $^{13}C$ NMR (CDCl$_3$) δ159.74, 138.68, 138.61, 138.24, 130.56, 129.98, 128.66, 128.62, 128.22, 128.04, 127.98, 127.86, 127.81, 114.15, 86.07, 85.36, 84.37, 79.17, 77.10, 75.70, 75.41, 75.14, 63.64, 55.18, 54.94, 45.92; FABMS (MNBA), m/z 584 ($M^+$+1), 476, 464, 466, 340, 121(100); $[\alpha]_D^{20}$ +53.5° (c 1.00 CHCl$_3$).

Anal. Calcd for $C_{36}H_{41}NO_6$: C, 74.07; H, 7.08; N, 2.40. Found: C, 74.21; H, 7.21; N, 2.34.

EXAMPLE 15

1-Amino-1,6-dideoxy-6-(hydroxymethyl)-2,3,4,5-tetrakis(phenylmethoxy)-myo-inositol (17a)

Scheme V:

Using similar reaction conditions, the title compound 17a is prepared from 10a and purified by flash chromatography.

EXAMPLE 16

1-Amino-1,2-dideoxy-2-(hydroxymethyl)-scyllo-inositol (16)

Scheme IV:

Hydrogenation of a solution of 15a in $CH_3OH$ containing Pd black for several days gives the title compound 16, which is purified by column or ion-exchange chromatography.

EXAMPLE 17

1-Amino-1,6-dideoxy-6-(hydroxymethyl)-myo-inositol (18)

Scheme V:

Similar reduction of 17a gives the title compound 18, which is purified by column or ion-exchange chromatography.

EXAMPLE 18

(−)-(3aα,4α,5β,6α,7β,7aβ)-Octahydro-7-hydroxy-1-methyl-4,5,6-tris(phenylmethoxy)-2,1-benzisoxazole (19)

Scheme VI:

To a stirred mixture of 989 mg (1.66 mmol) of 7b in 17 mL $CH_2Cl_2$ and 1.1 mL $H_2O$ was added 417 mg (1.84 mmol) of 2,3-dichloro-5,6-dicyano-1,4-benzoquinone (DDQ). After 17 h the mixture was diluted with aqueous $NaHCO_3$ and extracted twice with ether/EtOAc. The combined extracts were washed with dilute aqueous $NaHCO_3/Na_2S_2O_3$, brine, and dried ($MgSO_4$). The solution was concentrated in vacuo and resubjected to the reaction conditions two more times (3.51 mmol more DDQ used) to give 885 mg of orange-red semisolid. Flash chromatography eluting with 50/50 EtOAc/cyclohexane gave 107 mg (11%) recovered 7b and 453 mg (64% based on recovered 7b) of 19 as beige crystals. Recrystallization from first cyclohexane, then cyclohexane/ether gave 19 as fine white matted crystals: mp 142.5°–143.5° C.; IR (KBr) $\nu_{max}$ 3442, 2900, 2876, 1126, 1076, 1050, 740, 698 cm$^{-1}$; $^1H$ NMR (CDCl$_3$) δ7.37–7.24 (m, 15 H), 4.96 (d, 1 H, J=11.3 Hz), 4.92 (d, 1 H, J=10.7 Hz), 4.86 (d, 1 H, J=10.8 Hz), 4.75 (d, 1 H, J=12.1 Hz), 4.71 (d, 1 H, J=11.8 Hz ), 4.55 ( d, 1 H, J=11.5 Hz), 4.01 (t, 1 H, J=6.9 Hz), 3.77–3.64 (m, 2 H), 3.62–3.51 (m, 2 H), 3.47 (t, 1 H, J=8.9 Hz) 3.25 (bs, 1 H), 2.82 (s, 3 H), 2.61–2.47 (m, 1 H), 2.26 (dd, 1 H, J=11.0, 9.9 Hz); $^{13}C$ NMR (CDCl$_3$) δ138.52, 138.44, 138.07, 128.75, 128.62, 128.59, 128.11, 128.05, 128.01, 127.92, 127.88, 86.67, 85.94, 79.87, 75.85, 75.75, 73.74, 73.43, 70.23, 68.00, 49.79, 47.09; mass spectrum, m/z 516 ($M^+$+41), 504 ($M^+$+29), 476 ($M^+$+1, 100), 398, 386, 368, 107, 91 $[\alpha]_D^{25}$ −6.8° (c 1.03,CHCl$_3$).

Anal. Calcd for $C_{29}H_{33}NO_5$: C, 73.24; H, 6.99; N, 2.95; Found: C, 73.38; H, 7.13; N, 2.95.

EXAMPLE 19

(3aα,4α,5β,6α,7aβ)-Octahydro-1-methyl-4,5,6-tris(-phenylmethoxy)-2,1benzisoxazole (21)

Scheme VI:

A solution of 583 mg (1.23 mmol) of 19 in 5 mL THF (+2×3 mL THF rinse) is added with stirring to NaH [0.287 g (7.09 mmol) of 59% dispersion which was washed with three portions of pentane] under nitrogen. After 1.25 h at 25° C., the mixture is then heated to 50° C. for 0.25 h. $CS_2$ (2 mL) is added and the mixture is heated to reflux for 1 h; the mixture is allowed to cool to 30° C. and 0.44 mL (7.1 mmol) of $CH_3I$ is added. After 2 h, the mixture is poured into water and extracted with ether. The extracts are washed with water, brine, dried ($MgSO_4$), and concentrated in vacuo. Flash chromatography eluting with 20% EtOAC in cyclohexane gives the corresponding O-alkyl S-methyl dithiocarbonate 20.

A solution of 1.5 mmol of 20 in 15 mL dry toluene is added dropwise over 30 min to a stirred solution of 50 mL refluxing toluene, 2.3 mmol tributyltin hydride, and a catalytic amount of 2,2'-azobis-(2-methylpropionitrile). After the solution is refluxed for an additional 4–6 h, the solvent is removed in vacuo and the residue is dissolved in hexane and extracted with $CH_3CN$. The $CH_3CN$ extracts are washed with hexane and concentrated in in vacuo. Flash chromatography gives the title compound 21.

(22)

Hydrogenation of a solution of 21 in $CH_3OH$ containing Pd black in a Parr shaker for several days gives the title 1 compound where $R=CH_3$, $R^1=H$, and the hydroxymethyl substituent is beta which is purified by flash or ion-exchange chromatography.

Pseudodisaccharide 25

Using conditions similar to those used in the preparation of alcohol 19, 12b is converted to alcohol 23.

Scheme VII:

To a stirred suspension of 1.5 mmol NaH (previously washed in pentane) in 10 mL dry DMF under nitrogen is added 1.0 mmol 23. Bromide! (1.05 mmol) is added and the mixture is heated at 50°–90° C. until the alkylation is complete, usually 4–24 h. The mixture is then cooled, diluted with water, and extracted with EtOAc. The extracts are washed with water, brine, dried ($MgSO_4$), and concentrated in vacuo. The residue is purified by flash chromatography to give 24.

Hydrogenation of a solution of 24 in $CH_3OH$ containing Pd black for 2-5 days in a Parr shaker gives, after removal of the catalyst and solvent and flash or ion-exchange chromatography, the title compound 25.

The following Schemes correspond to the examples 1 through 19.

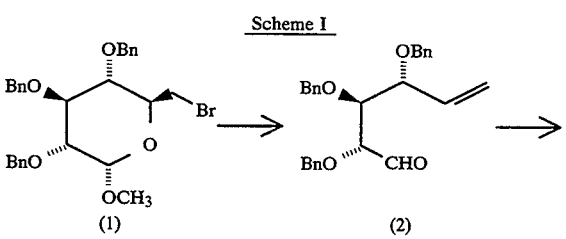

Scheme I

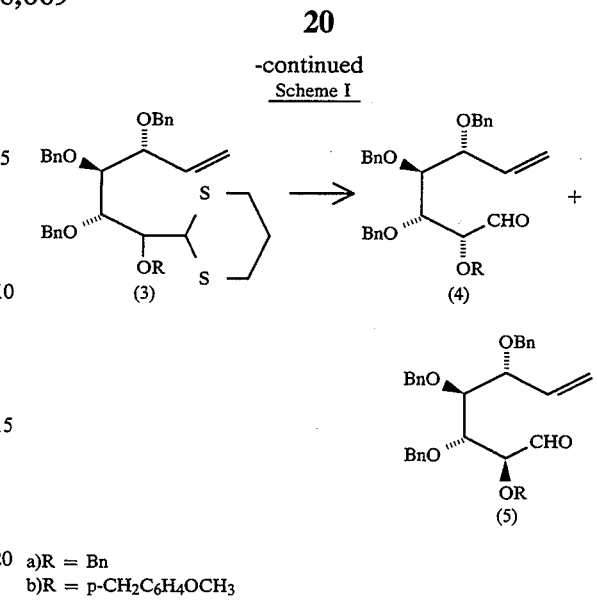

a) R = Bn
b) R = p-$CH_2C_6H_4OCH_3$

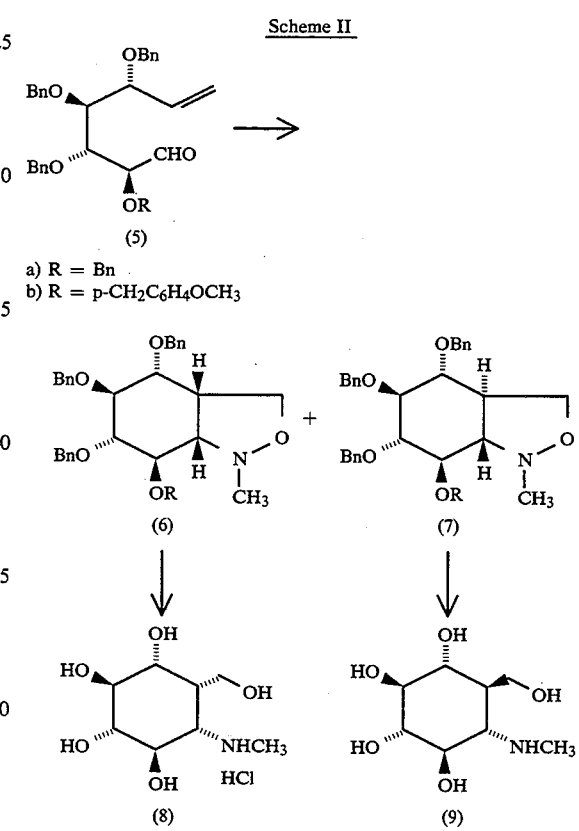

Scheme II a) R = Bn
b) R = p-$CH_2C_6H_4OCH_3$

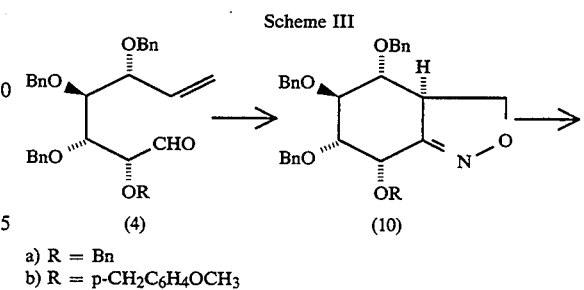

Scheme III a) R = Bn
b) R = p-$CH_2C_6H_4OCH_3$

-continued
Scheme III
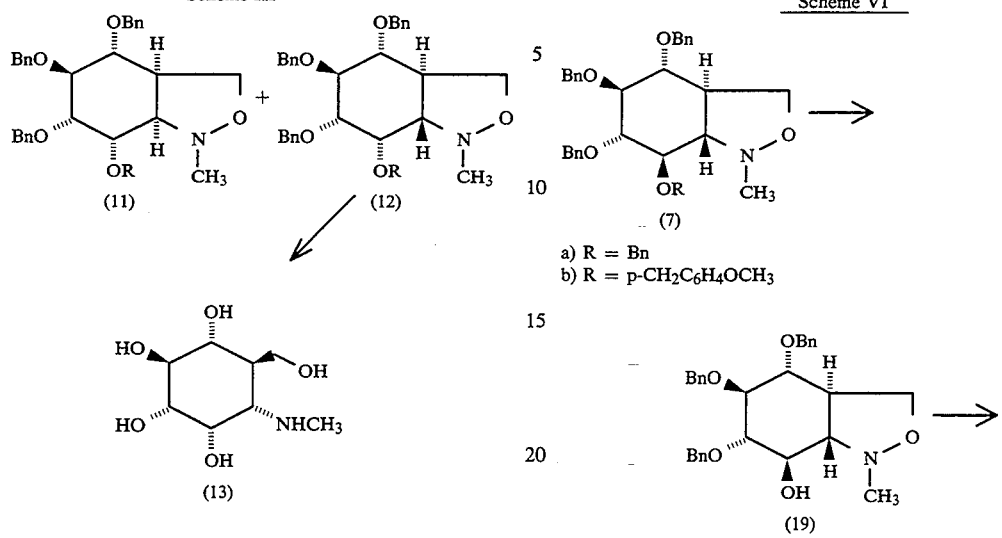
Scheme VI
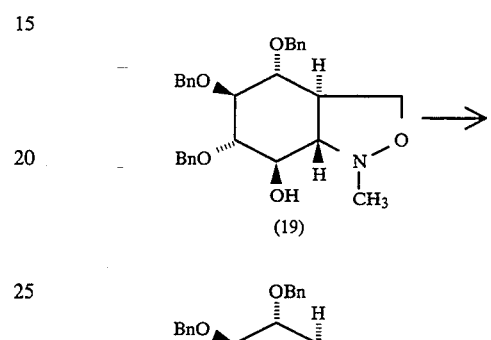
a) R = Bn
b) R = p-CH2C6H4OCH3
Scheme IV
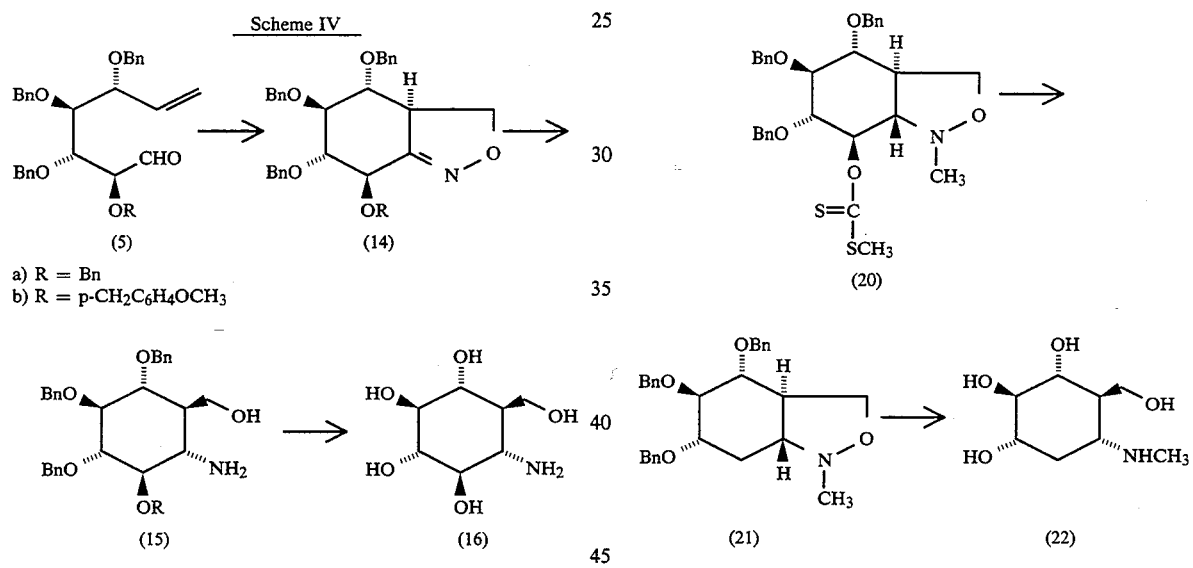
a) R = Bn
b) R = p-CH2C6H4OCH3
Scheme V
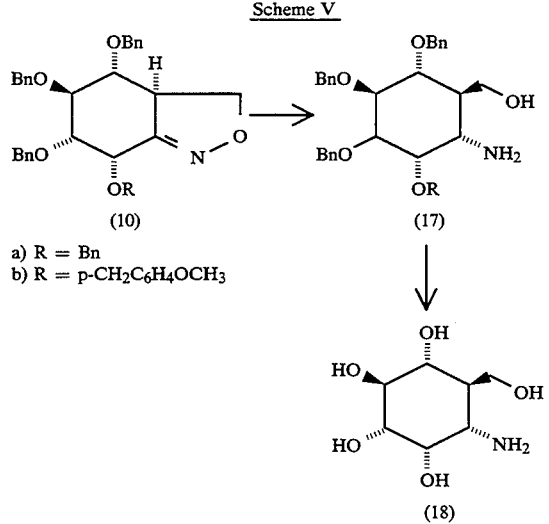
a) R = Bn
b) R = p-CH2C6H4OCH3
Scheme VII
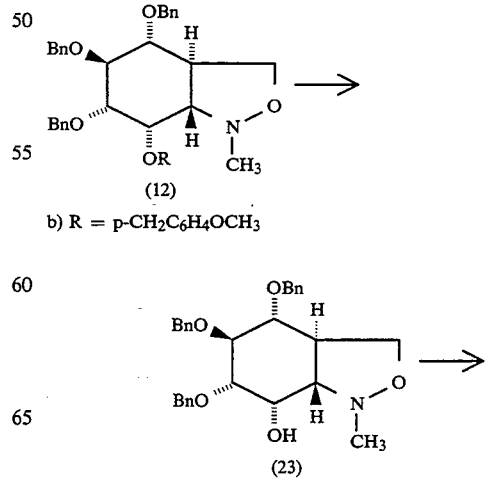
b) R = p-CH2C6H4OCH3

-continued
Scheme VII
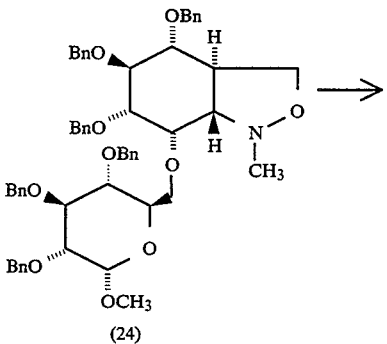
(24)
-continued
Scheme VII
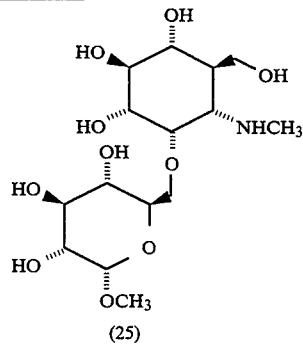
(25)
What is claimed is:
1. The compound 1,2-dideoxy-2-(hydroxymethyl)-1-(methylamino)-myo-inositol hydrochloride.
2. The compound 1,2-dideoxy-2-(hydroxymethyl)-1-(methylamino)-scyllo-inositol.
3. The compound 1,6-dideoxy-6-(hydroxymethyl)-1-(methylamino)-myo-inositol.
* * * * *

UNITED STATES PATENT AND TRADEMARK OFFICE
CERTIFICATE OF CORRECTION

PATENT NO. : 5,438,069
DATED : August 1, 1995
INVENTOR(S) : Robert A. Farr, Norton P. Peet It is certified that error appears in the above-identified patent and that said Letters Patent is hereby corrected as shown below:

Column 5, Line 23 patent reads: "trillate" and should read -- triflate --.

Column 5, Line 25 patent reads: "heating the a mixture" and should read -- heating a mixture --.

Column 5, Line 36 patent reads: "gylcosyl" and should read -- glycosyl --.

Column 7, Line 58 patent reads" vital" and should read -- viral --.

Column 9, Line 57 patent reads "with+brine" and should read -- with brine --.

Column 11, Line 56 patent reads "(d, 2 J=" and should read -- (d, 2 H, J= --.

Column 11, Line 60 patent reads "(d, H," and should read -- (d, 1 H, --.

Column 11, Line 64 patent reads "(t, 1 J=" and should read -- (t, 1 H, J= --.

Column 11, Line 66 patent reads "(m, 15 7.16(" and should read -- (m, 15 H), 7.16 --.

Column 12, Line 3 patent reads "(d, H, J=" and should read -- (d, 1 H, J= --.

Column 12, Line 33 patent reads "needle s" and should read -- needles --.

Column 12, Line 64 patent reads "75-96," and should read -- 75.96, --.

Column 14, Line 28 patent reads "(+)9b" and should read -- (+)-( --.

Column 14, Line 46 patent reads "more the mixture" and should read -- more of the mixture --.

Column 14, Line 50 patent reads "reisdue" and should read -- residue --.

Column 17, Line 42 patent reads "abetween" and should read -- between --.

UNITED STATES PATENT AND TRADEMARK OFFICE
CERTIFICATE OF CORRECTION

PATENT NO. : 5,438,069

DATED : August 1, 1995

INVENTOR(S) : Robert A. Farr, Norton P. Peet

It is certified that error appears in the above-identified patent and that said Letters Patent is hereby corrected as shown below:

Column 17, Line 53 patent reads "41.02" and should read -- 4.02 --.

Column 19, Line 30 patent reads "in in vacuo" and should read -- in vacuo --.

Signed and Sealed this

Sixteenth Day of April, 1996

*Attest:*

BRUCE LEHMAN

*Attesting Officer*       *Commissioner of Patents and Trademarks*